(12) United States Patent
Stringer

(10) Patent No.: US 6,340,592 B1
(45) Date of Patent: Jan. 22, 2002

(54) HUMAN CELL LINES

(75) Inventor: Bradley Michael John Stringer, Cardiff (GB)

(73) Assignee: CellFactors plc, Cambridge (GB)

( * ) Notice: Subject to any disclaimer, the term of this patent is extended or adjusted under 35 U.S.C. 154(b) by 0 days.

(21) Appl. No.: 09/694,203

(22) Filed: Oct. 23, 2000

Related U.S. Application Data

(62) Division of application No. 09/390,161, filed on Sep. 3, 1999, now Pat. No. 6,197,585, which is a continuation of application No. 08/836,440, filed as application No. PCT/GB95/02591 on Nov. 3, 1995, now abandoned.

(30) Foreign Application Priority Data

Nov. 8, 1994 (GB) .............................................. 9422523
May 24, 1995 (GB) .............................................. 9510555

(51) Int. Cl.[7] ......................... C12N 15/85; C12N 15/00; C12N 15/11; C07H 21/04
(52) U.S. Cl. ....................... 435/372; 435/325; 435/366; 435/375; 435/440; 435/455; 435/467; 536/23.1; 536/23.7; 536/23.72
(58) Field of Search .......................... 435/6, 69.1, 91.1, 435/440, 455, 467, 325, 366, 368, 372, 375, 320.1; 536/23.1, 23.7, 23.72

(56) References Cited

FOREIGN PATENT DOCUMENTS

| WO | WO 89/05862 | 6/1989 |
| WO | WO 94/12616 | 6/1994 |
| WO | WO 95/02687 | 1/1995 |

OTHER PUBLICATIONS

Lefebvre et al., Type X Collagen Gene Expression in Mouse Chondrocytes Immortalized by a Temperature–Sensitive Simian Virus 40 Large Tumor Antigen, The Journal of Cell Biology: 128 (1&2), pp. 239–245 (Jan. 1995).*
Stamps et al., Analysis of Proviral Integration in Human Mammary Epithelial Cell Lines Immortalized by Retroviral Infection with a Temperature–Sensitive SV40 T–Antigen Construct, Int. J. Cancer: 57, pp. 865–874 (1994).*
Abcouwer et al. (1989) Biotechnology 7:939–46.
Amsterdam (1988), Proc. Natl. Acad. Sci. USA, 85:7582–6.
Benoit et al. (1995) In Vitro Cell Dev. Biol. Anim. 31:174–7.
Cao et al. (1995) Bone 17:588.
Isom (1980), J. Cell Biol., 85:651–9.
Rhim (1985), Science, 227:1250–2.
Stamfer (1985), Proc. Natl. Acad. Sci. USA, 82:2394–8.
Stringer (1974), Developmental Brain Research, 79:267–74.
Verbruggen et al. (1993) Agents Actions Suppl. 39:267–72.
Vitry (1974), Proc. Natl. Acad. Sci USA, 71:3575–9.
Walker et al. (1995) Bone 17:565.
Yoakum (1985), Science, 227:1174–9.

* cited by examiner

Primary Examiner—Sean McGarry
Assistant Examiner—Mark L. Shibuya
(74) Attorney, Agent, or Firm—Klauber & Jackson

(57) ABSTRACT

The invention relates to a method for producing human cell lines and cell and cell-lines produced by such a method. The method comprising the use of precursor or undifferentiated cells treated with an immortalising agent which is susceptible to environmental conditions so as to provide for selective activation/deactivation of said immortalising agent and so selective activation of differentiation.

21 Claims, 15 Drawing Sheets

FIG. 14A
FIG. 14B
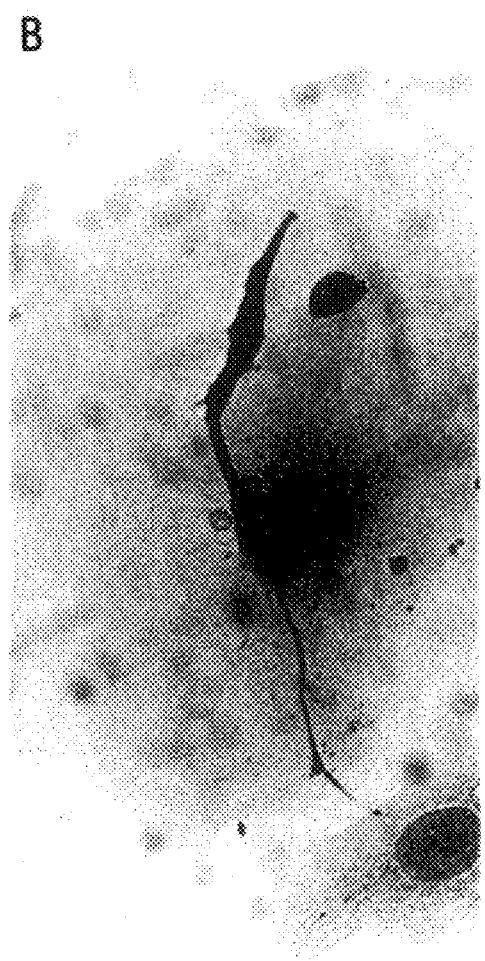

HUMAN CELL LINES

This application is a divisional of application Ser. No. 09/390,161, filed Sep. 3, 1999, now U.S. Pat. No. 6,197,585, which was a Continuation of application Ser. No. 08/836,440, filed May 8, 1997, now abandoned which was the National Stage of International Application No. PCT/GB95/02591, filed Nov. 3, 1995.

The invention relates to a method for producing human cell-lines; and cells and cell-lines when produced by such a method.

It is widely acknowledged that it would be advantageous to have in vitro cell models that simulate in vivo conditions. Ideally, the cell models should be able to propagate in culture, express specialised tissue functions and allow fundamental biological problems to be answered by a simple manipulation of the culture conditions. It is therefore not surprising to discover that researchers have spent many years trying to perfect in vitro cell models and in doing so they have discovered that normal differentiated cells generally do not proliferate in culture and often cease to express their specialised function. Indeed as far ago as 1965 Leonard Hayflick reported that when human lung fibroblast are observed in tissue culture the number of divisions these cells can undergo is limited. Similar observations have been made for a wide variety of tissue types and indeed it has been discovered that each type of tissue or cell undergoes a characteristic number of divisions before cell senescence or apoptosis. In order to circumvent what would seem to be age-related cellular death or senescence, researchers have investigated aberrant tumour cell-lines that are capable of growth in culture well beyond the normal level of growth encountered for a normal cell of the same tissue type, that is to say the cells are immortalised. Advantageously, these imortalised cells may retain the ability to express tissue-specific functions. It would therefore seem that immortalised cells may be favourable tools for in vitro investigations.

Indeed, historically the generation of cell-lines was founded on the observation that tumour cells do not exhibit apoptosis. Thus early cell-lines were obtained only as tumour cells or spontaneously immortalised variants of cells which grew readily in tissue culture. Subsequently, the discovery that certain viral oncogenes had the capacity to confer indefinite growth upon various normal cell types led to the rapid generation of non-human cell-lines by transfection of these immortalising genes directly into desired normal cell types in vitro. Immortalising genes can be introduced into cells by a variety of strategies such as transfection and retroviral mediated gene insertions. Thus the use of immortalising genes has facilitated the provision of a wide variety of non-human cell-lines from different tissues.

Over the past fifteen years it has been possible to produce non-human cell-lines retaining differentiated functions by transforming normal cells with chemical carcinogens (1), oncogenes (3), and tumour viruses (4,5). Workers have also attempted to produce human cell-lines retaining differentiated functions using oncogenes (2) and tumour viruses (6). However, although it is possible to produce human cell-lines that have retained some differentiated functions these human cell-lines do not go beyond a few replications before apoptosis or senescence. It therefore follows that such cell-lines are of little value for in vitro investigations.

In view of the considerable success experienced in producing non-human cell-lines it is both puzzling and frustrating that, so far, it has not been possible to use the same techniques to produce successfully human cell-lines, by the term successfully we mean immortalised cell-lines which retain their tissue specific characteristics. It will be apparent, that in the absence of immortalization and tissue specific characteristics cell-lines generated cannot be used as reliable in vitro cell models.

It is interesting to note that the production of immortalised murine cell-lines can be provided using any of the above techniques, whereas it is not possible to provide immortalised human cell-lies. The difference may, in part, be related to the life expectancy of the organism from which the cells derive. For example, the life expectancy of a mouse is approximately 2 years whereas the life expectancy of a human is approximately 70–80 years and therefore it is possible that because of this significant difference in life expectancy there may be more stringent regulation of human cell replication and this stringent regulation may, in part, be responsible for the profound general lack of success in producing differentiated human cell-lines.

Our invention is based on a surprising discovery, we have found that, contrary to expectations, it is possible to produce an immortalised human cell-line which expresses tissue specific functions when the method of the invention is practised, which method involves the use of immature, undifferentiated or precursor cells. Although such cells have been used before to study differentiation—no one has before realised that such cells can be used routinely to provide immortalised human cell-lines that express the tissue specific functions seen in the mature differentiated phenotype.

It is therefore important to note that although undifferentiated cells have been used to provide cell-lines for the purpose of studying the differentiation process where one would expect to start with an undifferentiated cell if one wanted to study the process leading to differentiation, no-one has thought to use undifferentiated cells as a source for providing a cell-line when one simply wants to study the differentiated cell. Rather, it is customary to take a differentiated cell and then imortalised the differentiated cell with a view to producing a human cell-line. It is therefore interesting to note that the method of the invention goes against conventional teaching.

It is also interesting to note that when undifferentiated cells are used to produce human cell-lines for the purpose of studying the process of differentiation and when a controllable immortalising agent has been used such as the SV40 large-tumour T antigen the method has always involved the switching on and off of the immortalising agent at preselected intervals along the differentiation pathway so that at these predetermined intervals the products of differentiation can be identified with a view to establishing markers for mapping the differentiation pathway. In contrast, the method of the invention concerns the use of an undifferentiated cell which is allowed to progress continuously towards terminal differentiation with a view to investigating the differentiated cell therefore, once again, it can be seen that the method of the invention goes against conventional teaching.

It can therefore be seen that there is a need to provide immortalised human cell-lines which can be used as in vitro cell models and it is therefore an object of the invention to provide a method that produces such cell-lines; and cells and cell-lines when produced by such method.

According to a first aspect of the invention there is therefore provided a method for producing human cell-lines, the method comprising;

a) immortalising a human undifferentiated or precursor cell of a given tissue type using an immortalising agent which includes or has associated therewith a control means whereby activation of the control means terminates immortalisation and allows differentiation of the undifferentiated or precursor cell, b) culturing said immortalised cell in order to produce a homogeneous population of human cells, c) activating the control means in order to terminate immortalisation and activate differentiation, and d) allowing differentiation of said cells so as to produce fully differentiated cells of said given tissue type.

It can be seen from the above that the method is characterised by the use of undifferentiated or precursor cells in order to produce a desired fully differentiated human cell-line. It follows that the choice of the undifferentiated or precursor cell will determine the nature of the cell-line. Thus for example, an osteoblast cell-line will be provided by the use of bone marrow stromal cells; an osteoclast cell-line will be provided by the use of haemapoietically derived osteoclast precursors, a heart cell-line will be produced by the use of myocardial precursor cells; a kidney cell-line will be provided by the use of kidney cell precursor cells; a muscle cell-line will be provided by the use of muscle precursor cells; a skin cell-line will be provided by the use of epithelial precursor cells; a liver cell-line will be provided by hepatocyte precursor cells; a lung cell-line will be provided by lung cell precursor cells; and T & B Lymphocytes will be provided be the use of lymphocyte stem cells. It can therefore be seen from the afore examples that the nature of a given cell-line can be determined having regard to the type of differentiated or precursor cells used in the method of the invention.

We have surprisingly found that the use of undifferentiated or precursor cells in the method of the invention provides for an immortalised human cell-line that retains the functional characteristics associated with the cell type from which the cell-line was derived. We have therefore, uniquely, been able to provide human cell-lines for use as in vitro cell models. Our cell-lines are immortal and reliable.

In a preferred embodiment of the invention immortalisation is achieved by using conventional transfection techniques and preferably the immortalising agent is an immortalising gene that is an oncogene, more preferably still, the immortalising agent is a viral oncogene which can be stably integrated into the host cell genome.

Ideally, the immortalisation agent is a construct, preferably a retroviral construct, including an oncogene which oncogene may be virally derived or a human derived oncogene. Any known oncogene may be used such as myc, ras, src, etc.

Alternatively, immortalisation may be effected using physical or chemical means For example, immortalisation may be effected by exposing said cell to radiation or chemicals which are known to promote cell division well beyond the normal level encountered when a cell is not exposed to said physical or chemical means.

In a preferred embodiment of the invention the control means is responsive to environmental conditions such as temperature, pH or ionic concentrations.

In yet a further preferred embodiment of the invention the immortalising agent and control means are integrated, that is to say the immortalising agent is itself controllable. Thus the immortalisation agent and the control means may comprise, for example, a single entity such as a temperature sensitive oncogene. Alternatively, the immortalisation agent and the control means may be two independent entities but in either case, ideally activation/deactivation of the control means has ideally a direct effect such, as in one embodiment, a reciprocal effect on the immortalisation agent. For example, when the control means is activated the immortalisation agent is deactivated. Conversely, when the control means is deactivated the immortalisation agent is activated. Ideally control can be achieved having regard to culture or environmental conditions, for example, in the preferred embodiment of the invention, the immortalising agent is temperature sensitive and the control is thus represented by a temperature sensitive switch so that at about, above or below a first given temperature the immortalising agent is activated so as to immortalise the selected cell type, but at, about, or above a second temperature the immortalising agent is deactivated and in this instance immortalisation terminates and differentiation is allowed to proceed in order to provide a homogeneous population of cells of a given cell type.

Preferably the immortalising agent is the SV40 T antigen which is permissive, that is to say the viral gene is expressed in an active form, at 33° C. and non permissive, that is to say the viral gene is expressed in an inactive form at 39° C. thus cells immortalised using this agent are temperature sensitive for differentiation.

Uniquely, our cells, when transformed using SV40 T antigen differentiated at the non permissive temperature and survived crisis a condition which is typically followed by apoptosis. In surviving crisis our cells were immortalised. We believe that the feature of immortalisation is due to the use of the undifferentiated or precursor cell in the method of the invention.

In a preferred embodiment allowing differentiation of said cells comprises culturing said cells in the presence of a differentiating agent for example to produce osteoblasts, said differentiating agent is Vitamin $D_3$, ideally in the presence of Vitamin K.

In an alternative preferred embodiment allowing differentiation of said cells comprises culturing said cells in the presence of a differentiating agent for example to produce osteoblasts said differentiating agent is dexamethasone.

In a preferred embodiment allowing differentiation of said cells comprises culturing said cells in the presence of a differentiating agent for example to produce adipocytes, said differentiating agent is rabbit serum or an extract thereof.

In yet a further preferred embodiment of the invention said human cell-line also includes a safety feature which allows for selective disabling or destruction of said cell-line. This safety feature is of advantage where the cell-line is to be used for the purpose of transplantation or is otherwise, whether it be permanently or temporally, attached to, or administered to, or stored in, an individual. The safety feature allows the cell-line to be selectively disabled, and by this we mean rendered harmless, or destroyed, in instances where the cell-line is thought likely to, or is shown to, have the potential to become tumourigenic in vivo, or is thought to be in anyway harmful to an individual.

Preferably the safety feature comprises a gene whose products acts either directly or in-directly to disarm or destroy the cell-line. For example, the gene may be a gene which in the presence of certain agents such as for example anti-viral agents, produces a cytotoxic product. One example of such a gene would be the gene encoding viral thymidine kinase (vTK). This gene avidly converts prescribed anti-viral drugs into cytotoxic intermediates. Another example of a gene which could be used as a safety feature is the cytosine deaminase (CD) gene. The product of this gene renders cells vulnerable to the effects of 5-fluorocytosine and results in cell death.

In a preferred embodiment of the invention the safety feature is expressed in conjunction with the immortalising oncogene. This arrangement is preferred because it means that the immortalising gene is unlikely to be expressed in the absence of the safety feature and visa versa. Our co-pending patent application GB 94 22236.1 teaches how a vector can be produced which provides for co-expression of the safety feature which could be linked with the immortalising oncogene.

In one preferred embodiment of the invention the safety feature gene is placed downstream of the immortalising oncogene and ideally next to but 3' to, for example, a poliovirus derived internal ribosomal entry site sequence (IRES). This arrangement ensures that the promoter/enhancer elements(s) controlling the transcription of the immortalising oncogene, equally, control the transcription of the safety feature.

It will be apparent to those skilled in the art that other arrangements may be provided in order to enable co-expression of the immortalising oncogene and the safety feature and it is not intended that the above example should be construed in a fashion which limits the scope of protection provided by the application.

According to a further aspect of the invention there is provided a method for the production of osteoblast cells comprising exposing the Human Cell-lines in accordance with the invention to a differentiating agent.

Preferably said differentiating agent is Vitamin $D_3$, ideally in the presence of Vitamin K.

Preferably said differentiating agent is dexamethasone.

According to a further aspect of the invention there is provided a method for the production of adipocytes from Human Cell-lines in accordance with the invention comprising using a differentiating agent.

Preferably said differentiating agent is rabbit serum or an extract thereof.

According to a yet further aspect of the invention there is provided a method for identifying an agent responsible for stimulating differentiation to produce adipocytes the method comprising exposing said Human Cell-line in accordance with the invention to said agent and observing any characteristics of the differentiated phenotype.

Preferably said agent is produced by extraction from rabbit serum using a separation technique, for example, ionic separation, chromatography, protein precipitation etc.

According to a futher aspect of the invention there is provided the use of rabbit serum to produce adipocytes from either a cell-line, preferably a bone marrow cell-line, or at least one precursor cell, preferably a bone marrow precursor cell.

According to a further aspect of the invention there is provided a composition which contains an agent which affects a differentiation process. Preferably said composition is a pharmaceutical composition.

Preferably said agent stimulates the process of differentiation.

Alternatively said agent blocks or prevents differentiation, which differentiation results in the provision of adipocytes.

The bone marrows of osteoporotic patients often contain fatty tissue which is often referred to as fatty marrows. This observation, along with our recognition that the same human bone marrow stromal cells can derive both adipocytes and osteoblasts allows us to propose that osteoporosis may be a consequence of perturbations in bone marrow stromal cell differentiation to the osteoblast lineage, in favour of adipocyte formation. The information provided here, therefore, gives direction to the man skilled in the art to look at this differentiation process for the provision of pharmaceutical agents capable of controlling it. For example:- separation agents from the separation (ionically, HPLC, alternative chromatography, protein precipitation and separation etc.) of normal rabbit serum can be used to determine the agent or agents inducing differentiation to the adipocyte lineage These agents can be used to recognise the intracellular signl transduction pathway involved in the differentiation process; and the subsequent development of agents to effect this pathway. It is envisaged that this information may also lead to the identification of agents for controlling obesity.

According to a further aspect of the invention there is provided cells or cell-lines produced in accordance with the method of the invention. Accordingly there is provided at least one homogenous population of immortalised human cells provided with means to terminate immortalisation such that a homogenous population of differentiated human cells is provided.

According to a yet further aspect of the invention there is provided use of immature, undifferentiated or precursor cells to produce terminally differentiated human cell-lines that express tissue-specific functions.

The invention will now be described by way of example only with reference to a human bone cell-line and with reference to the following figures wherein.

FIG. 1 shows the effects of temperature and Dexamethasone ($5 \times 10^{-7}$M) on alkline phosphatase activity on human bone marrow stromal clone 7 cells.

Table 1 shows the effects of temperature and Dexamethasone on mRNA expression in an immortalised clone of human bone narrow stromal cells.

Figure 6:
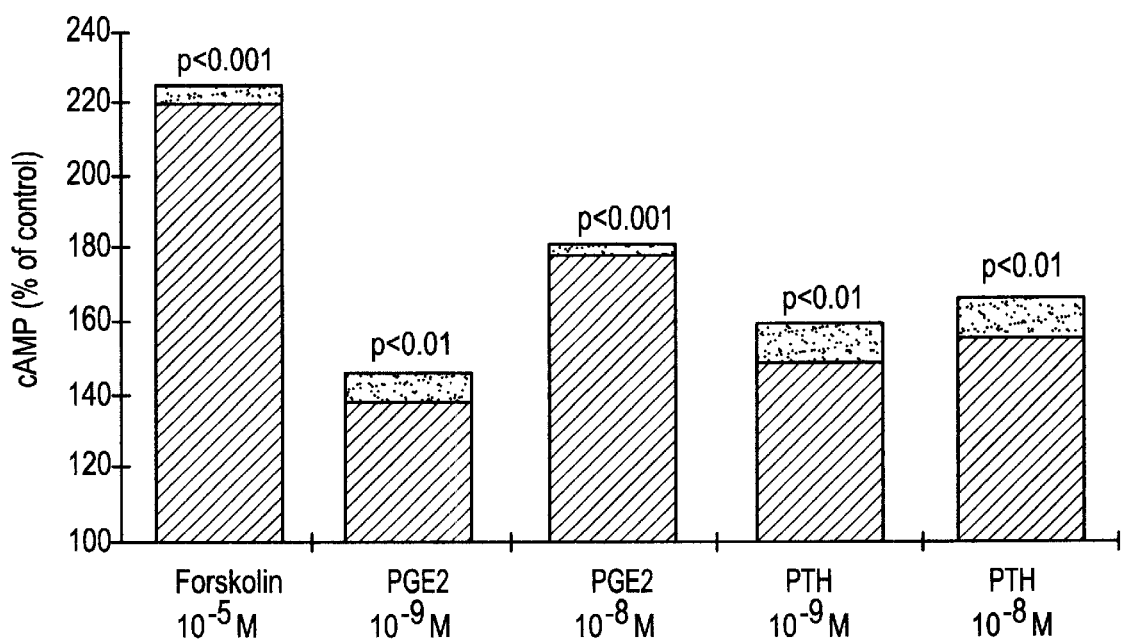

FIG. 6 is a bar chart which shows the effects of various agonists on cAMP levels of clone 7 cells. Cells were penetrated with 1 mM IBMX for 5 minutes, and then treated with the appropriate dose of agonist for 20 minutes. cAMP levels were quantitated using an E.I.A., and the amounts of cAMP for each treatment was compared with the control (IBMX only) and expressed as a percentage.

Figure 7:
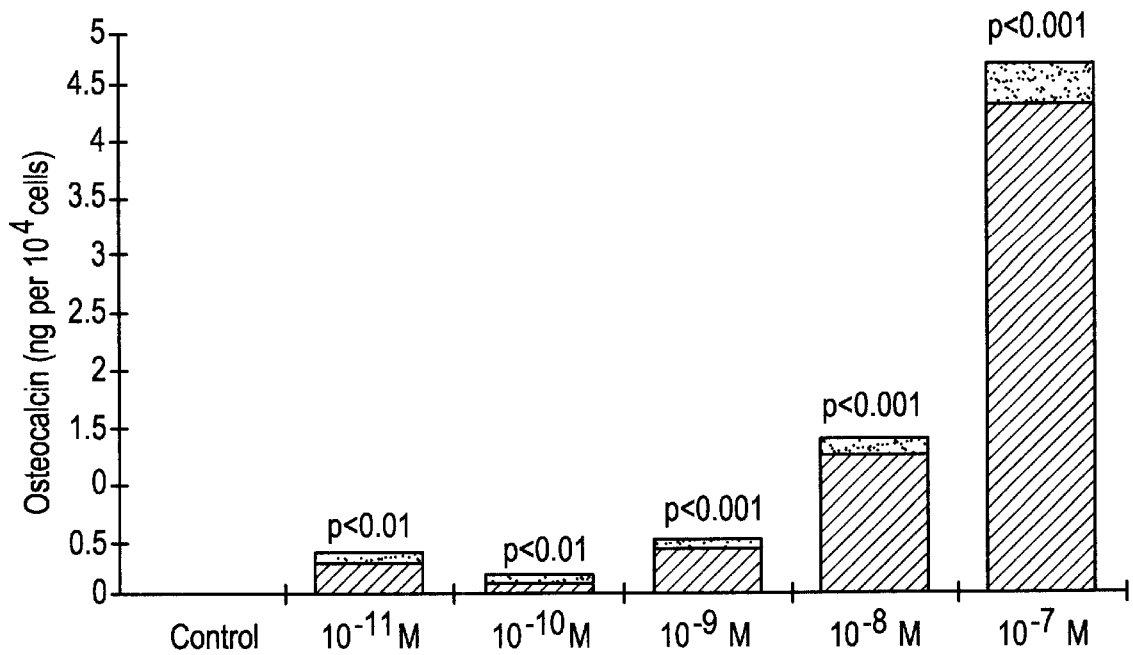

FIG. 7 is a bar chart which shows the Osteocalcin synthesis of clone 7 cells over a 4 day period. Cells were treated with various concentrations of 1,25(OH)$_2$D$_3$ in the presence of vitamin K for 4 days. The media was then removed and the amounts of osteocalcin measured using an R.I.A. and osteocalcin levels normalised to ng osteocalcin per 10000 cells.

Figure 8:
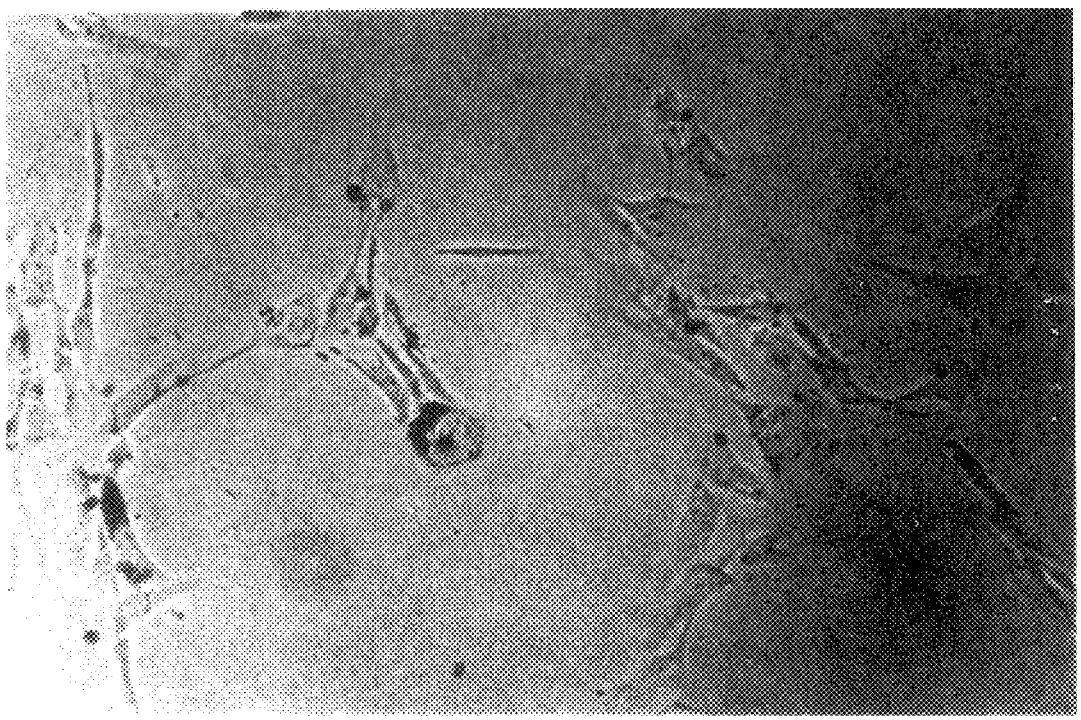
Figure 9:
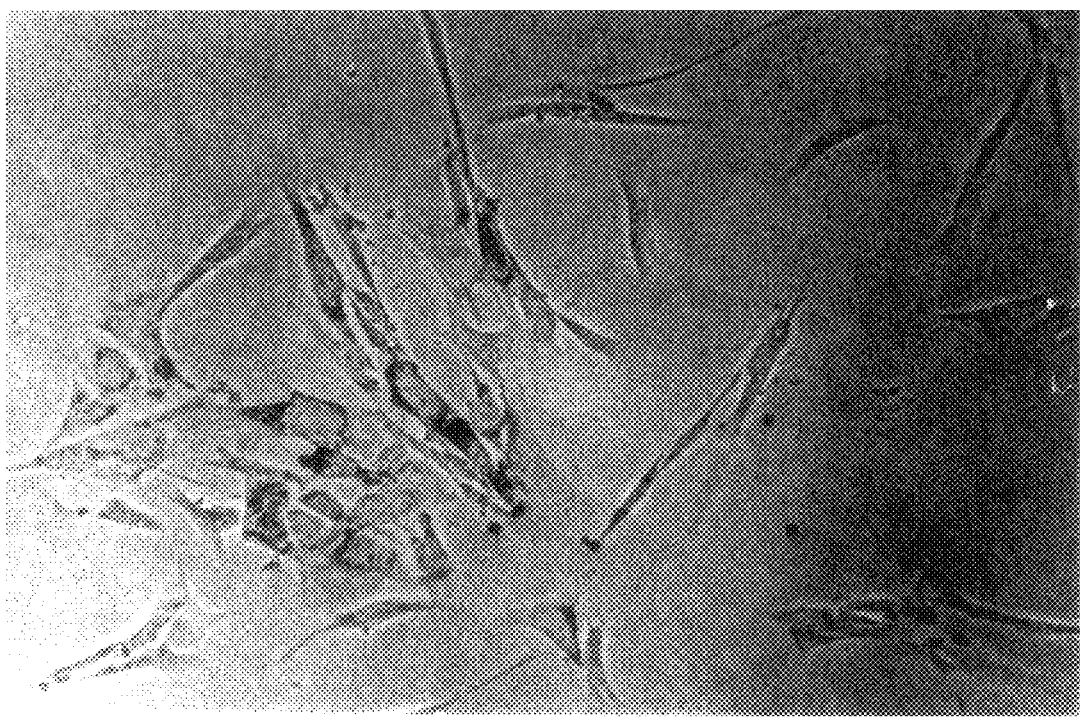
Figure 10:
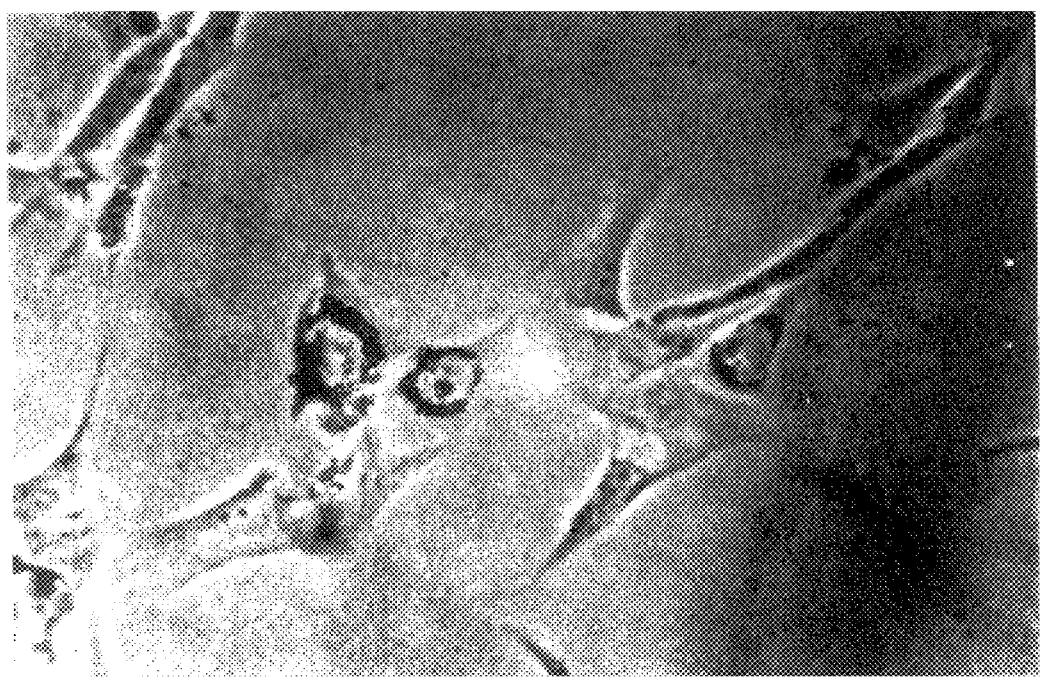
Figure 11:
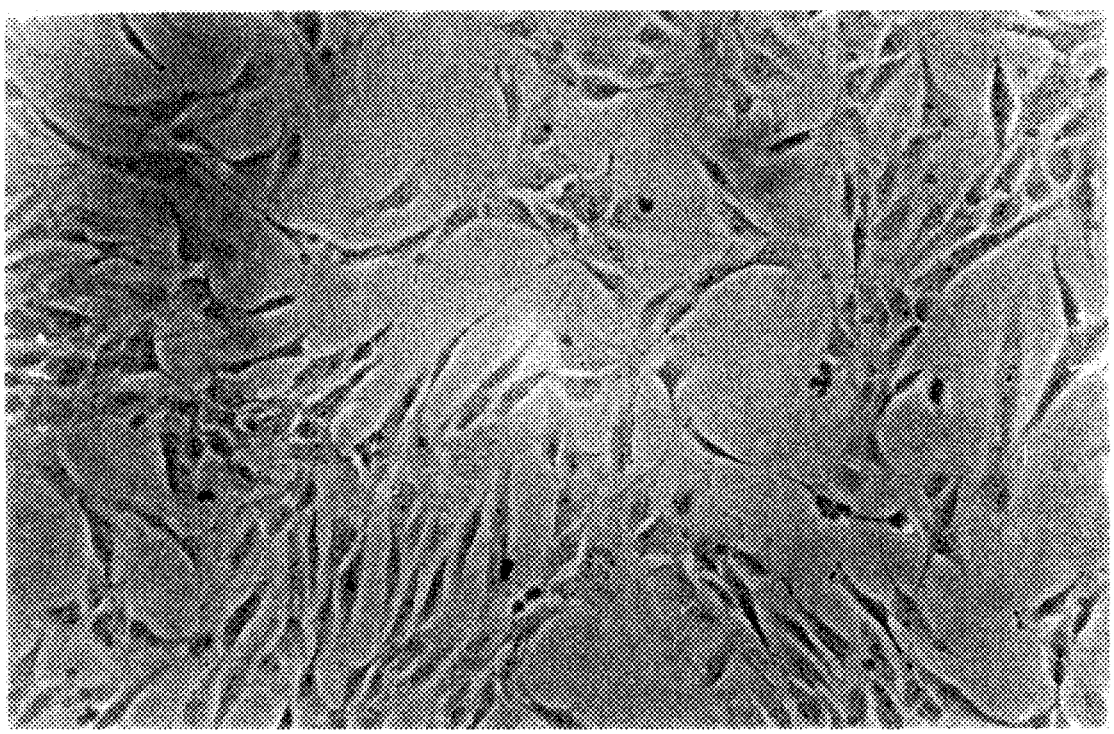

FIGS. 8, 9, 10 & 11 are photographs which depict Oil-red-O staining of the immortalised bone marrow stromal cell-line, clone 7. FIGS. 8 and 9 show cells after 3 days treatment with 10% rabbit serum at 39° C. at ×100 magnification. FIG. 10 shows cells after 3 days treatment with 10% rabbit serum at 39° C. at ×200 magnification. FIG. 11 shows cells after 3 days treatment with 10% foetal bovine serum at 39° C. at ×100 magnification.

Figure 12:
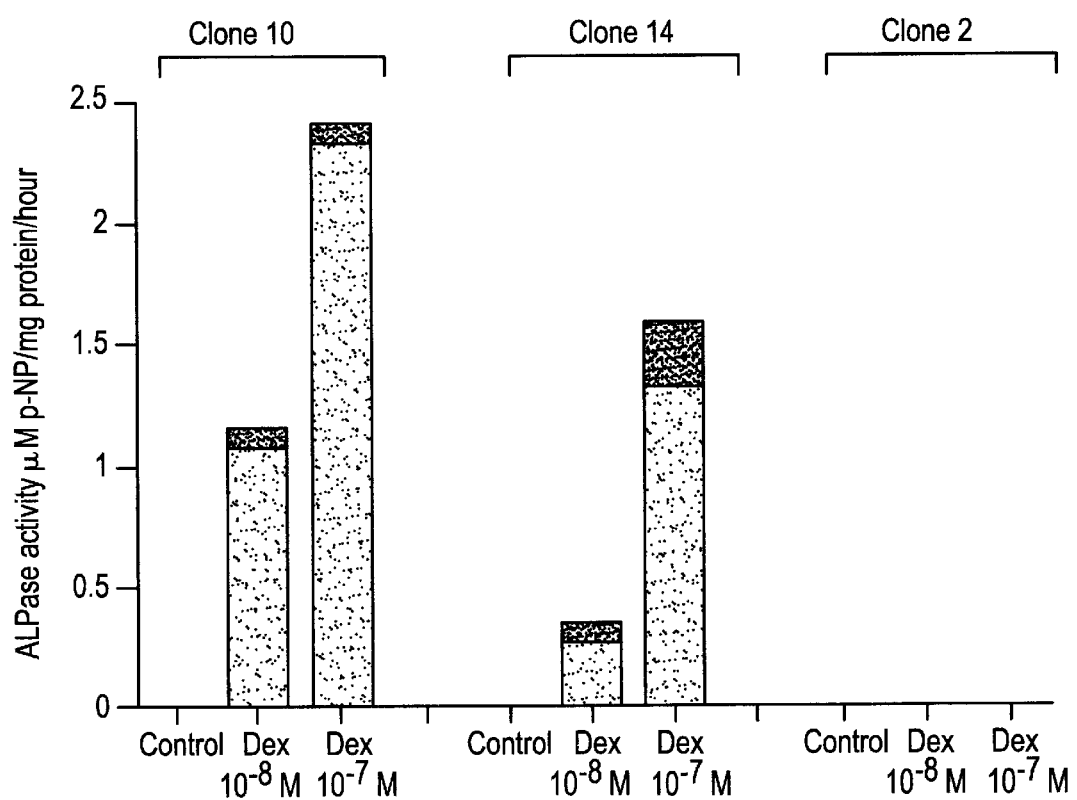

FIG. 12 is a bar chart showing the effects of Dexamethasone on alkaline phosphatase activity in three immortalised human foetal cell clones at 39° C. for 7 days.

Figure 13:
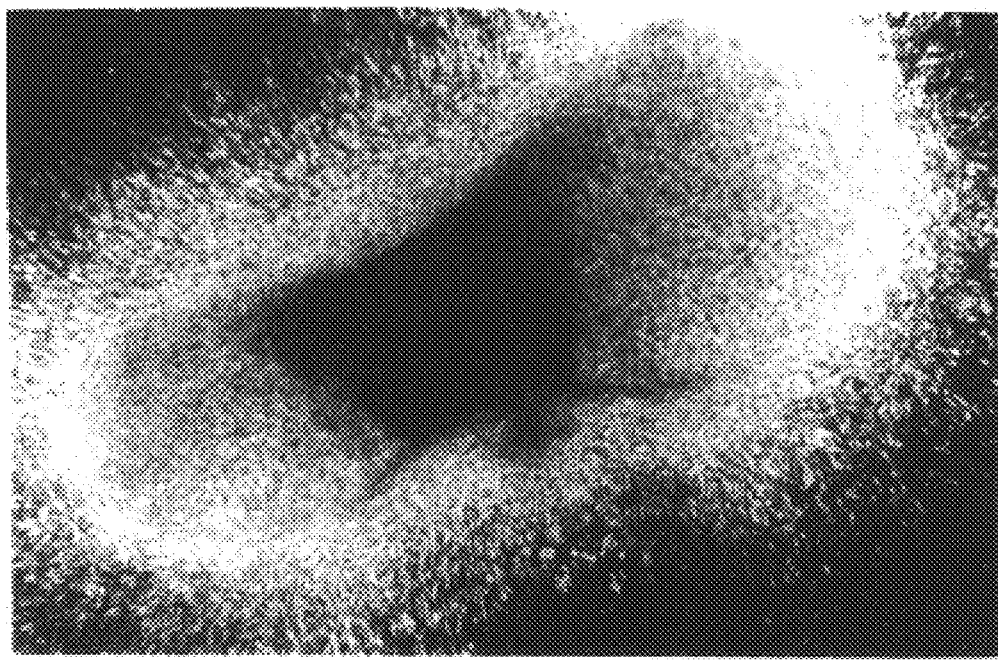

FIG. 13 shows a femur derived from a human foetus 7–9 weeks of gestation and of approximately 600 μm in length.

FIGS. 14 A–C show immunohistochemical analysis of cells in a culture of a human cortical precursor immortalized with temperature-sensitive SV40T oncogene.

IMMORTALISATION OF BONE MARROW STROMAL CELLS

Human trabecula bone was immersed in medium comprising EMEM+10% foetal calf serum, plus L-grlutamine, plus 1×penicillin/streptomycin (all from Sigma Chemicals) and agitated to release the bone marrow cell population. After 24 hours, to enable the stromal cell population to adhere to the tissue culture flask (Costar, UK Ltd) surface, the medium was replenished to remove the non-adherent cell population. The adherent cell population was then transfected with a temperature sensitive mutant of the simian vis-40 derived large tumour M antigen using retroviral transduction, Any standard method of transfection of this sequence (alone with linkage to an appropriate promoter to drive its expression eg LTR promoter) would suffice, such as calcium phosphate DNA precipitation, electroporation or micro-injection, but retroviral transduction was chosen for its simplicity of use.

Culturing of the Immortalised Cells in Order to Produce a Homogenous Population of Cells In short, amphotropically packaged retroviral particles comprising this construct and a resistance marker to geneticin, G418 (kindly donated by Dr M. O'Hare, Institute of Cancer Research, Royal Marsden Hospital, Lincoln's Inn, Sutton, Surrey and also Professor P. Gallimore, The University of Birmingham, UK) was added to the medium together with polybrene (Sigma Chemicals) to a final concentration of 0.8 mg/ml. The viral titre was adjusted to give a low transduction efficiency of 0.0002% producing an average of 20 immortalised cell colonies per flask, each colony derived from a single cell. Two hours after virus addition, the culture medium was replaced with fresh medium. Cultures were maintained at 33° C., the permissive temperature for the active form of the SV40-T oncogene product. Five days after transduction, geneticin was added to the medium (0.4 mg/ml) for a further 10 days to eradicate cells which had not incorporated the retroviral vector.

Differentiation of said Cells

Between 14–20 days after transduction, individual colonies of replicating cells were identifiable. Clones were selected on the basis of being well separated from other replicating colonies, the cells in each colony numbering between 100–1000 cells. These were picked by ring cloning and expanded up to near confluence in 75 cm2 flasks (Costar, UK Ltd) which equated to approximately 22 divisions from a single cell, prior to freezing stocks down in aliquots. We have been growing samples of cells generated in this way in culture for well over a year and have some clones which have undergone more than 60 divisions ($10^{18}$ cells), Samples were also used for cell characterization and to determine that they possessed the ability to differentiate into mature osteoblast-like cells. Differentiation was effected by exposing the cells to the oncogene's non-permissive temperature (39° C.) and a differentiating agent such as dexamethasone or Vitamin $D_3$.

Provision of Human Cell-lines Including a Selectively Controllable Safety Feature Another preferred embodiment of the invention is the preparation of homogeneous populations of cells by retroviral transduction, but also incorporating a safety feature which enables the cells to be selectively destroyed if needs be. This would be seen as an advantage when such cells are used for transplantation into patients to alleviate the symptoms of e.g. neurodegenerative disorders, osteoporosis or osteoarthritis, for example.

The safety feature would allow the transplant to be selectively destroyed in, for insace, situations where the transplanted material may become tumourigenic in-vivo. Ways in which this could be done are numerous and well known to the man skilled in the art. For example, the addition of the viral thymidine kinase (vTK) gene, under the control of an appropriate promoter, to the ts-SV40-T transduced cells would mean that cells expressing SV40-T, would also be expressing the vTK gene. This gene avidly converts prescribed anti-viral driugs such as ganciclovir or aciclovir, into cytotoxic intermediates which kill the cell in which it is expressed. Such a suicide gene would be a particular advantage for graft eradication if necessary.

Another example of such a molecular safety switch is the cytosine deaminase (CD) gene. Cells which express CD become sensitive to 5-fluorocytosine and die in its presence whereas cells not expressing the CD gene remain unaffected. The preferred invention should not be seen as limited to vTK and CD as negative selection markers, as the man skilled in the art could easily replace these with alternatives.

Another aspect of the preferred invention, whereby a safety mechanism is put into the cells to serve as a negative selection component, would be to have the safety component expressed in conjunction with the immortalising oncogene. This would be particularly preferred as it would mean that the immortalising gene is unlikely to be expressed in the absence of the negative selection safety mechanism and vice versa. The man skilled in the art of vector construction would be quite capable of making such a construction and the reader is referred to one of our other patent applications, GB 94 22236.1 in this respect. For example, the negative selection gene (e.g. CD or vTK) could be placed downstream of the immortalising gene and next to but 3' to e.g. a poliovirus derived internal ribosomal entry site sequence (IRES). In this way the same promoter/enhancer element(s) controlling the transcription of the immortalising gene would, equally, control the transcription of the safety element. This is because they would be transcribed as one complete unit, including the IRES sequence which would sit in between them. The IRES sequence allows the translation of sequences downstream of it which code for a separate protein from the sequence 5' of it. The ability to provide such a vector, once given the idea, is well within the range of expertise of the man skilled in the art.

Experiments to Show Functional Characteristics of the Human Bone Marrow Stromal Cells Characterisation of clones that we have produced using this method, and which have been grown for over a year in culture, has shown that the cells retain the features expected of an osteoblast precursor lineage and under stimulation to differentiate, they potentiate the phenotype of the mature osteoblast.

Differentiated bone marrow cells which are responsible for the production of bone are known as osteoblasts. A recognised indicator of osteoblast activity is a measure of alkaline phosphatase activity—an enzyme active in the production of bone or the minerals hydroxyapatites.

Figure 1:
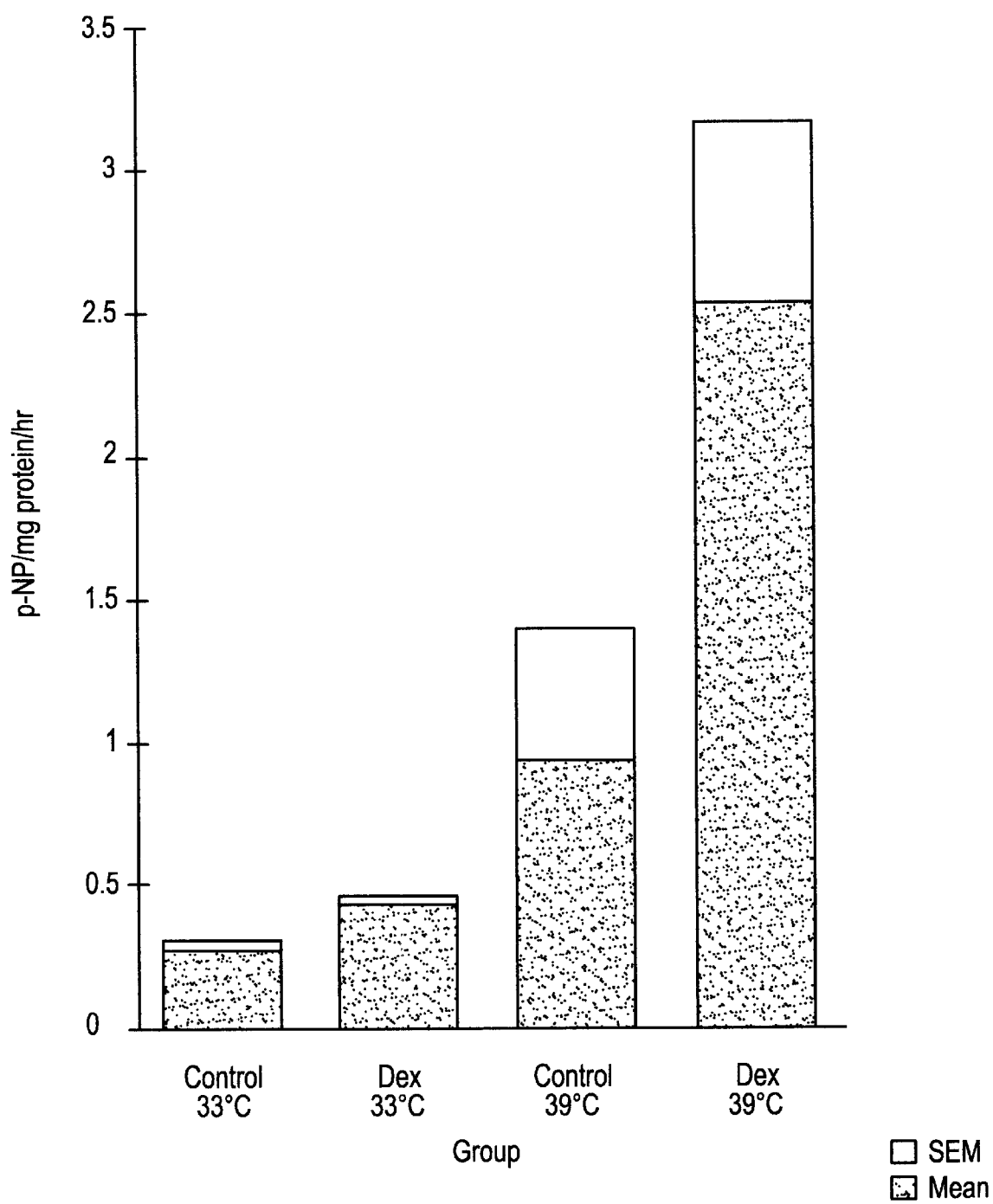

In FIG. 1 it can be seen that immortalised bone marrow stromal cells at the permissive temperature of 33° C. exhibit an alkaline phosphatase activity of approximately 0.3p-NP/mg protein/HR. Exposure of these immortalised cells at the permissive temperature of 33° C. to dexamethasone—a differentiation factor—results in only a slight increase in alkaline phosphatase activity ie to approximately 0.5p-NP/mg protein/HR.

In contrast, the same immortalised cells at a non permissive temperature of 39° C. in the absence of any differentiating agent show an enhanced amount of alkaline phosphatase activity. Indeed, alkaline phosphatase activity increases to approximately 0.9p-NP/mg protein/HR. It would therefore seem that at the non permissive temperature of 39° C. differentiation takes place and thus enzyme activity characteristic of the differentiated cell type increases. A further increase in this activity is observed when immortalised bone marrow stromal cells are cultured at the non permissive temperature of 39° C. and in addition exposed to dexamethasone—a differentiating agent. Under these conditions alkaline phosphatase activity increases to approximately 2.5p-NP/mg protein/HR. This activity is approximately 5 times higher than in cells exposed to the differentiating agent dexamethasone at the permissive temperature of 33° C.

This data shows that cells immortalised in accordance with the method of the invention can be selectively made to differentiate at the non permissive temperature of 39° C. and differentiation results in the formation of cells having functional characteristics akin to that of osteoblasts, in other words differentiation results in the production of osteoblasts.

Summarily, at the oncogene's non-pernissive temperature (39° C.), and, in the presence of differentiating agents such as dexamethasone or Vitamin $D_3$, they substantially up regulate their alkaline phosphatase activity (FIG. 1).

The data in Table 1 similarly shows that bone marrow stromal cells immortalised in accordance with the method of the invention can be made to differentiate into functional osteoblasts. The table shows mRNA expression in an immortalised clone of human bone marrow stromal cells. Investigations were undertaken in order to identify agents typically characteristic of an immortalised condition. These agents are shown on the far left hand side of Table 1. At the permissive temperature of 33° C. immortalised human bone marrow stromal cells expresed all agents except interleukin 3 and interleukin 4. The use of dexamethasone at this temperature showed the same pattern of agent expression however there was a slight reduction in interleukin 1 Alpha and interleukin 1 Beta and GM-CSF expression and a slight increase in TNF alpha expression.

In contrast, at the non permissive temperature of 39° C. there was a marked difference in the pattern of agent mRNA expression. As before, there was no expression of interleukin 3 or interleukin 4. However, in addition, there was also no expression of the previously expressed intereukin 1 alpha, interleukin 1 beta, interleukin 8, GM-CSF and TNF alpha. However, interleukin 6 and collagen 1 are still expressed at this temperature. At the non permissive temperature of 39° C. dexamethasone increased the expression of interleukin 6 and interleukin 8 but reduced the expression of collagen 1.

If the above 2 patterns of expression, that is the expression of the immortalised cell and the expression of the differentiated cell, are compared with the expression of osteoblast-like cells it can be seen that those cells grown at the non-permissive temperature of 39° C., that is to say those cells exposed to differentiating conditions, exhibit an expression pattern almost identical to that of osteoblast-like cells. The only difference being that the osteoblast-like cells express interleukin 8 whereas the differentiated human bone marrow stromal cells only express this agent in the presence of dexamethasone.

The above data shows that immortalised human bone marrow stromal cells can be made to differentiate at 39° C. and when made to differentiate exhibit a range of characteristics, by way of protein expression, almost identical to that of osteoblast-like cells. This data therefore suggests that the immortaised human cell-line can be made to differentiate to produce osteoblasts.

Summarily, our studies of cytokine and growth factor expression show the cells in the undifferentiated state express IL-1alpha and IL-1beta along with IL-6, IL-8, GM-CSF and TNFalpha, as well as the matrix protein collagen type I. When treated with dexamethasone or Vitamin $D_3$ for a period of up to 7 days, IL-1alpha, beta expression is lost along with GM-CSF, TNFalpha and collagen type I. In addition IL-6 and IL-8 expression is maintained in the presence of both Vitamin $D_3$ and dexamethasone. Furthermore, no expression of IL-3 or IL4 is seen at any stage. Interestingly, the cytokine/growth factor profile that we have identified in these cells after treatment with differentiating agents reflects the profile we see of differentiated human osteoblast-like cells in primary culture (Table 1).

In addition, we have found that if the transduced cell clones are left at the oncogene's non-permissive temperature in the presence of differentiating agents eg (Vitamin $D_3$ or Dexamethasone) and 10 mM of B glycerol phosphate, the cultures express osteocalcin protein and mineralise after 20 days (FIGS. 2, 3, 4 and 5).

Figure 2:
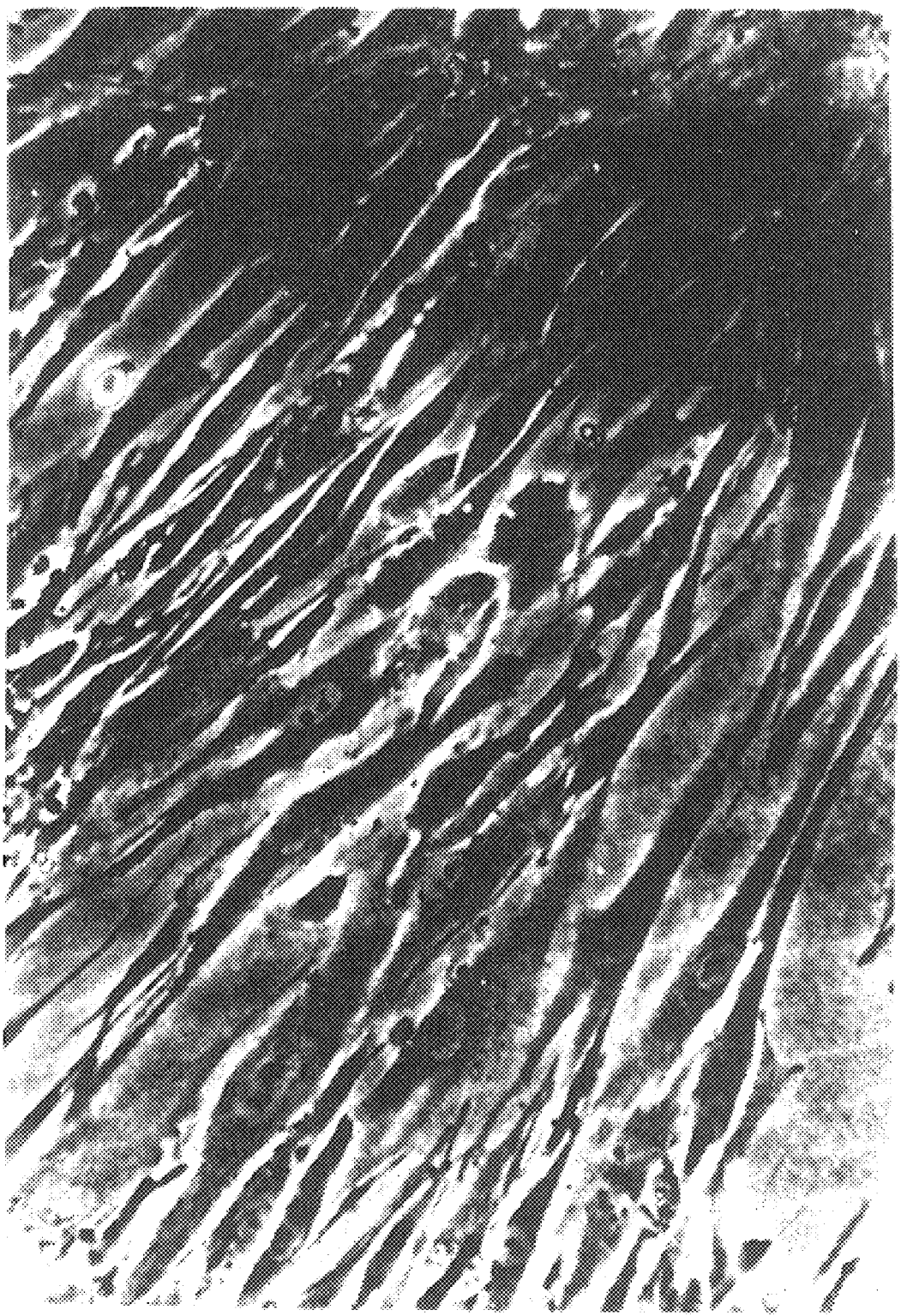
FIG. 2 shows staining of an untreated immortalised human bone marrow stromal cell clone at 33° C.×100.

FIG. 2 shows undifferentiated immortalised human bone marrow stromal cells at 33° C. It can be seen that there is no evidence of mineralisation or osteocalcin protein in this figure.

Figure 3:
FIG. 3 shows staining of an immortalised human bone marrow stromal cell clone at 39° C. treated with dexamethasone $5 \times 10^{-7}$M at 39° C.
Figure 4:
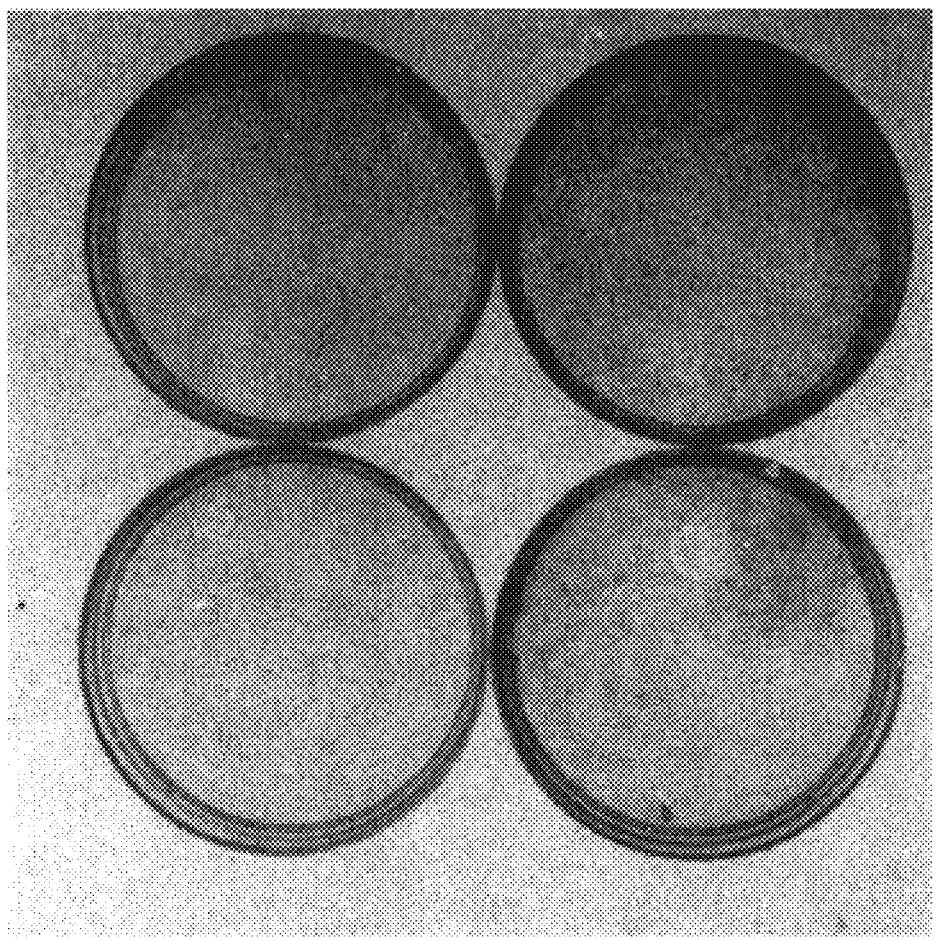
FIG. 4 shows staining of an immortalised human bone marrow stromal cell clone and mixed population with and without Dex $5 \times 10^{-7}$M at 39° C.

In contrast, FIG. 3 shows immortalised human bone marrow stromal cells when exposed to differentiating agents at the oncogene's non-permissive temperature of 39° C. Mineralisation is clearly evident. This feature represents the differentiated cell and thus indicate that the immortalised human bone marrow stromal cell clones of the invention can be made to differentiate fully so as to express the mature phenotype.

FIG. 4 shows again staining of an immortalised human bone marrow stromal cell clone and a mixed population of immnortalised cells both in the presence and absence of dexamethasone at 39° C. It can be seen that relatively little differentiation occurs at 39° C. in the absence of a differentiating agent. However, in the presence of a differentiating agent a significant increase in differentiation occurs and thus mineralisation is observed. Further, it can be seen that the phenotypic characteristics are observed both in the mixed population and in the single clone.

Figure 5:
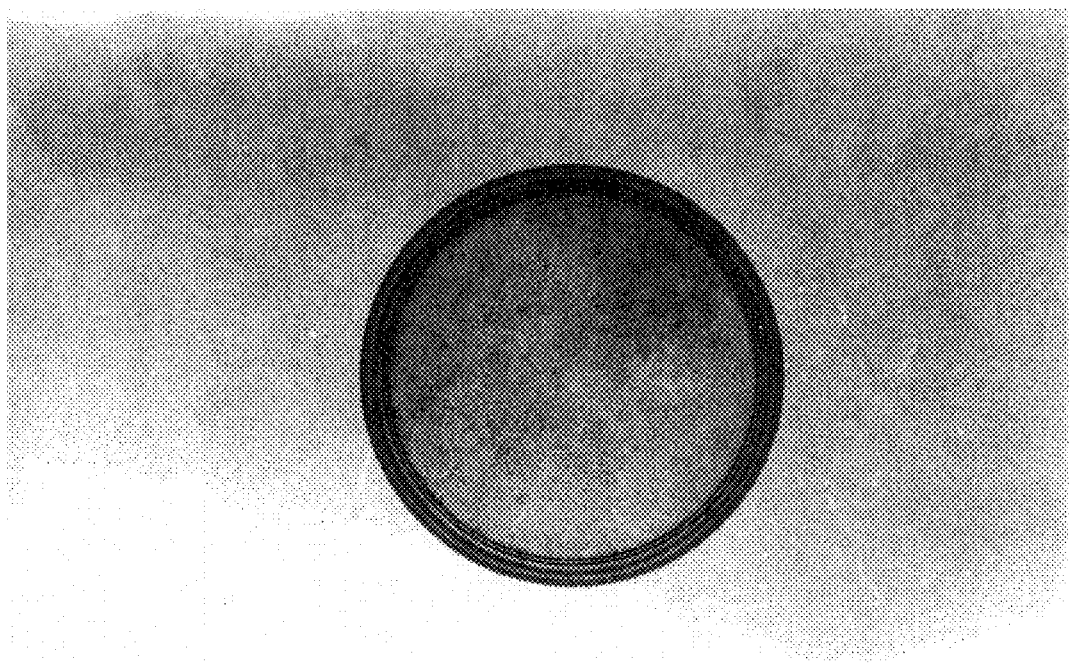
FIG. 5 shows staining of an immortalised human marrow stromal cell clone with Dex $5 \times 10^{-7}$M at 39° C.

FIG. 5 shows staining of a single clone under a differentiating conditions, that is at 39° C. and in the presence of the differentiating agent dexamethasone.

The data in FIGS. 2, 3, 4 and 5 indicates that cells can be made to fully differentiate such that they express the phenotype of a mature osteoblast.

FIG. 6 shows further evidence that bone marrow stromal cells, immortalised and then made to differentiate in accordance with the invention, produce differentiated cells phenotypically similar to osteoblasts. FIG. 6 shows the cyclic-AMP response of the differentiated cells to two agonists, namely prostaglandin E2 (PGE2) and parathyroid hormone (PTH). The data indicate a clear cyclic-AMP response to the agonists which is typical of the response of cells of the osteoblast lineage.

Yet further evidence that immortaised bone marrow stromal cells after undergoing differentiation form osteoblast progenitor cells is demonstrated by FIG. 7. FIG. 7 shows the effect of Vitamin $D_3$ in the presence Vitamin K, on the expression of osteocalcin protein in our immortalised human bone marrow stromal cells as determined by radioimmunoassay (Nichols Institute). In the absence of Vitamin $D_3$ there is no expression of osteocalcin (see 'control'), the marker of osteoblast differentiation. The bone cell differentiating agent Vitamin $D_3$, however, induces a dose dependent expression of osteocalcin.

Therefore, it can be seen from this data, together with our mineralisation date (FIGS. 2 to 5), and also our alkaline phosphatase data (FIG. 1), that the differentiated cells are osteoblast progenitor cells.

FIGS. 8, 9, 10 & 11 show a series of photographs, and provide evidence that our immortalised osteoblast precursor cells can, under alternate conditions, also differentiate to become adipocytes. This is important since: it underlines the fact that we truly have precursor cells; and it fits with central dogma, as it is thought, that bone marrow stromal cells also derive adipocytes—hence early precursors from the bone marrow may also have the capacity to go down either a bone or an adipocyte differentiation pathway depending on the nature of stimulation.

FIGS. 8, 9 and 10 clearly shows that rabbit serum, or at least one agent in rabbit serum, triggers a differentiation process which produces adipocyte cells as shown by the red staining. FIG. 11 shows that, in the absence of rabbit serum no red staining occurs, indicating no adipocyte formation. This result provides further evidence that early precursor cells from bone marrow may have the capacity to differentiate to produce adipocyte or osteoblast cells.

The photographs depict Oil-red-O staining (a marker of fat cells) of our immortalised bone narrow strormal cell-line, clone 7. This occurs after three days treatment with medium containing normal rabbit serum (but not foetal bovine serum) showing that the bone marrow stromal cell population, which in the presence of Vitamin $D_3$ and/or dexamethasone commits to an osteoblast differentiation pathway, is capable of becoming an adipocyte when cultured under appropriate conditions. This confirms the precursor status of our immortalised cells.

In addition to the above staining we have also demonstrated changes in specific gene expressions. Firstly, the expression of lipoprotein lipase (LPL), a known early marker for adipocytes, can be identified within a few days of rabbit serum treatment. Secondly, type I collagen expression, a marker of the osteogenic lineage, disappears after a few days treatment with normal rabbit serum. The expression of LPL and the disappearance of type I collagen, therefore, provide further support to the bipotential nature of the human bone marrow stromal cells that have been generated. Thus we believe we are using genuine precursor cells in order to make our human cell-lines.

FIG. 12 depicts alkaline phosphatase levels in a series of three human bone marrow stromal cell-lines that have been derived from foetal bone. None have alklaine phosphatase activity at basal levels (control) but when stimulated with dexamethasone for 7 days, two of the three clones (clones 10 and 14) can be induced to express alkaline phosphatase activity. The key point is that in the absence of dexamethasone, no alkaline phosphatase activity is detectable. Thus we have not selected these precursors on the basis of alkaline phosphatase expression. Both clones 10 and 14 will mineralise after 14–20 days in culture in the presence of dexamethasone and phosphate. The remaining clone, clone 2, cannot be induced to express alkaline phosphatase activity by treatment with dexamethasone, nor will it mineralise in culture.

FIG. 13 shows a femur derived from a human foetus of 7–9 weeks of gestation and of approximately 600 µm in length. The femur has been cultured for a period of 14 days to allow the expansion of replicating cell populations which can be seen streaming from all regions of the femur. This was prior to cell immoitalisation by retroviral temperature sensitive oncogene transduction. The figure therefore shows the nature of the cell population that was used to produce some of the cell-lines of the invention.

Longevity of the Human Bone Marrow Stromal Cell-line

Using the method of the invention we have surprisingly found that our human cell-line successfully differentiates to produce functional cells which cells avoid crisis and thus apoptosis. The cell-line therefore continues to survive and our current human bone marrow stromal cell-line has passed through 40 divisions over a period of one year producing $10^9$ cells. The cell-line continues to survive and moreover the cells of the line continue to show functional characteristics typical of the tissue type of the differentiated cell. Thus we have been able to produce an immortalised human cell-line comprising differentiated cells that retain their functional characteristics.

Chondropiron genitor Cell-lines

As well as generating precursor cells for the osteogenic lineage, which are capable of differentiating down an adipocytic route, we have also produced chondroprogenitor cell-lines which, in the presence of differentiatine agents such as dexamethasone, will become hypertrophic chondrocytes.

Cell-lines have been generated by retroviral temperature sensitive oncogene transduction as described above using human foetal tissue as source matery (having first obtained ethical approval).

Some of these cell-lines have the capacity to mineralise in culture in the absence of any factors which induce differentiation, and, consequently, are already differentiated. In addition, though, some cell-lines exbit no basal levels of activity related to differentiated cell types. To show that these undifferentiated cell-lines could potentiate hypertrophic chondrocytes, we added the differentiating agent, dexamethasone, to the culture medium of cell clones derived by single cell cloning after immortalisation. After several days treatment with dexamethasone we demonstrated that some of the clones would express type X collagen, a marker for hypertrophic chondrocytes. Type I collagen was not expressed in these cells clearly showing that they were not of osteoprogenitor orign The cells were also responsive to $1,25(OH)_2D_3$ and expressed high levels of alkaline phosphatase activity, two further markers of the hypertrophic chondrocyte-like phenotype. Also, when the cells are left in monolayer culture for 10–14 days at 39° C., the oncogene's non-permissive temperature, and in the absence of added β-glycerophosphate, the cultures mineralise.

Again, this data clearly shows that undifferentiated or true precursor cells are being used to provide human cell-lines and that the origin of the precursor cells determines the phenotype of the differentiated cell-line.

Neural Cell-lines

In another embodiment of claim 1, neural tissue for immortalization was dissected from human foetal material at 8–12 weeks of gestation; this is close to the optimum age for immortalizing (via retroviral transduction) forebrain cells such as striatal neurones and some cortical neurones, because they have not yet undergone their final replication in vivo. They are thus are still capable of incorporating the retroviral oncogene into their genome and stably expressing it.

Seven regions were dissected from the 8–12 weeks foetal CNS—cortex, striatum, hypothalamus, rostroventral mesencephalon, caudoventral mesencephalon, medullary brainstem and the dorsal and ventral horns of the spinal cord. Dissociated cells from these regions were plated onto a number of different substrates (gelatin/polylysine, fibronectin, uncoated plastic) and incubated in a defined medium (Stringer et al., 1994). The cells were transduced by our usual method (Stringer et al., 1994) with an amphotropic virus (PA317-CMV48T)(from P. Gallimore, University of Birmingham, UK) encoding the controllably expressed oncogene (ts-SV40T) linked to a geneticin resistance marker (G418).

Since human CNS neural precursors exhibit a degree of intrinsically driven replicative potential in fibroblast growth factor (FGF)-containing medium, it was considered advantageous to allow both transduced and non-transduced cells alike to expand in the same culture flasks. In this way, if further samples of fresh human material became unavailable, it would be possible simply to retransfect the existing cells in order to generate more clones. Accordingly, once the mixed cells had reached confluence, the cultures were passaged, and a proportion frozen for possible later use.

The passaged cells were treated with geneticin to eradicate non-transduced cells, and after 10–12 days, small clones were apparent. Single G418-resistant, transduced cells from each clone were taken for expansion. In order to achieve this, we have developed a method of driving the cells both to survive better and to replicate more rapidly during the early, critical stages of expansion, by co-culturing them with supporting cells kept as feeder layers in cell-well inserts (Corning). Once the clonal cells numbered about a one or two hundred, they become self-supporting, with a noticeably increased mitotic rate. At this stage, the inserts containing the supporting cells were no longer required, and could be removed. We have now isolated several homogeneous clones in this way, although we still have many hundreds of heterogenous, mixed clones either frozen or continuing to expand. The clones expanded from single cells have been growing continuously since their initial culturing in May 1994.

Differentiation of a clone from the human cortex has been analyzed in most detail. Cells from this clone were plated onto 24-well plates and expanded at the oncogene's permissive temperature of 33° C. for 2–3 days. The cells were then grown at the non-permissive temperature of 39° C. in the presence of a variety of agents and other cell types. These included nerve growth factor, ciliary neurotrophic factor (CNTF), brain-derived neurotrophic factor, glial cell line-derived neurotrophic factor (GDNF), FGF, epidermal growth factor, platelet-derived growth factor, retinoic acid and different sera. After 14 days under these conditions the cells were fixed and screened immunohistochemically with a battery of cell-type specific antibodies such as neurofilament, neurone-specific enolase, glial fibrillary acidic protein, myelin-oligodendrocyte glycoprotein, nestin, vimentin and CD11b (labelling microglia). We found a neuronal phenotype was apparent both morphologically and immunochemically after the precursor clone had been incubated in the presence of glial-derived neurotrophic factors (see FIG. 14). Incubation with CNTF led to an astrocyte-like phenotype instead. Interestingly, although the precursor cells are homogeneous, having been expanded from a single cell, it appears that they can give rise to at least two different phenotypes under each given set of conditions. This sort of multipotentiality is in contrast to the multipotentiality seen with our rat-derived raphe clones, where one set of conditions results in a homogeneous neuronal phenotype being expressed (Stinger et al, 1994). Presumably the multiple phenotypes of the cortical clone reflect the early stage of cortical development at which the precursors were isolated, when cells have a less restricted commitment to individual differentiation pathways. Nestin and vimentin were also identified from this clone.

Figure 14C:
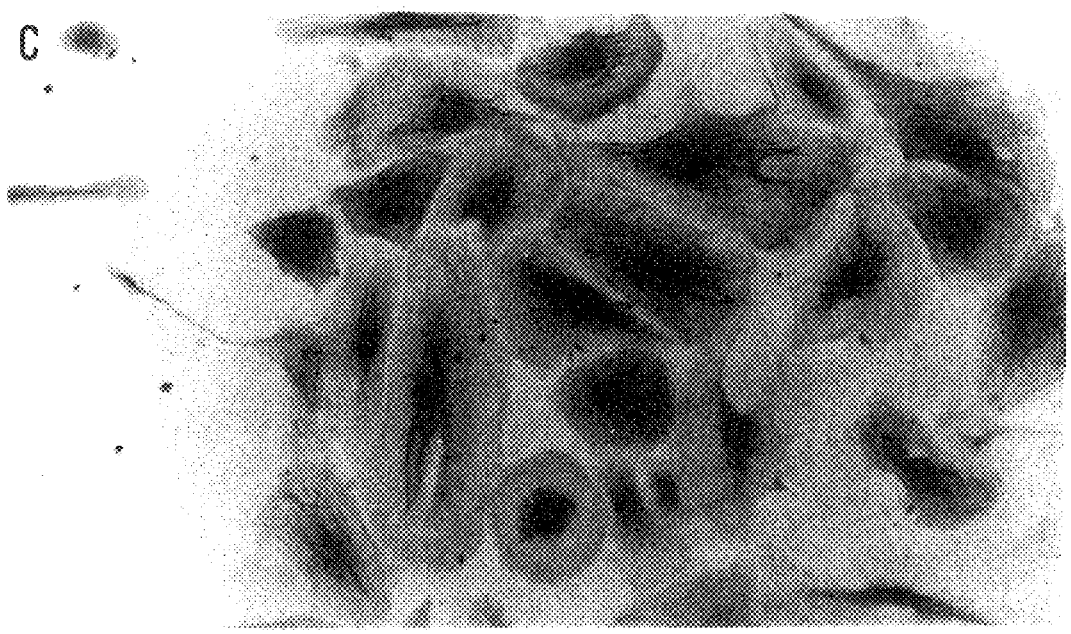

In FIG. 14A the homogeneous precursor cells were incubated at the non-permissive temperature of the oncogene (39° C.) in the presence of glial derived neurotrophic factor, and allowed to differentiate. Some of the precursors (arrowed) developed a phase-bright morphology, and exhibited neurone-specific enolase immunoreactivity, a characteristic marker of neurones. Higher magnification is shown in FIG. 14B. Other cells, however, adopted a different phenotype. Incubation with CNTF lead to an astrocyte-like phenotype instead. The same precursors were incubated with ciliary neurotrophic factor instead (please see FIG. 14C). They now no longer displayed any NSE-immunopositivity. However, meshworks of GFAP-immunoreactive fibres (a marker for astrocytes) became prominent, most cells being positive.

Interestingly, we have therefore shown that undifferentiated, or precursor cells can be used to produce human cell-lines with considerable success and that the nature of the differentiated phenotype of such cell-lines is determined by the nature of the precursor cell and, in some instances, the nature of the differentiating agent to which the human cell-line is exposed.

References

1. Stampfer M R, Bartley J C 1985. Induction of transformation and continuous cell-lines from normal mammary epithelial cells after exposure to benzo[a]pyrene. Proc Natl Acad Sci USA 82:2394–2398.

2. Yoakuum G H, Lechner J F, Gabrielson E W, Korba B E, Malan-Shibley L, Willwy J C, Valerio M G, Shamsuddin A M, Trump B F, Harris C C 1985. Transformation of human bronchial epithelial cells transfected by Harvey'ras oncogene. Science 227:1174–1179.

3. Amsterdam A, Zauberman A, Meir G, Pinhasi-Kimhi O, Suh B S, Oren M 1988. Contransformation of granulosa cells with simian virus 40 and Ha-RAS oncogene generates stable lines capable of induced steroiogenesis. Proc Natl Acad Sci USA 85:7582–7586.

4. Vitry F, Camier M, Czernichow P. Benda P, Cohen P, Tixier-Vidal A 1974. Establishment of a clone of mouse hypothalamic neurosecretory cells synthesising neurophysin and vasopressin. Proc Natl Acad Sci USA 71:3575–579.

5. Isom H C, Tevethia J, Taylor J M 1980. Transformation of isolated rat hepatocytes with simian virus 40. J Cell Biol 85:651–659.

6. Rhim J S, Jay G, Arnstein P, Price F M, Sanford K K, Aaronson S A 1985. Neoplastic transformation of human epiermal keratinocytes by AD12-SV40 and Kirsten sarcoma viruses. Science 227:1250–1252.

7. Stringer B. M. J., et al., Raphé neural cell immortalized with a temperature-sensitive oncogene, Developmental Brain Research 79:267–274, 1974.

What is claimed is:

1. A method for producing a human hypertrophic chondrocyte cell line comprising:
   (a) immortalizing a human undifferentiated or precursor chondroprogenitor cell using an immortalising gene which includes or has associated therewith a control means whereby activation of the control means terminates immortalisation and allows differentiation of the undifferentiated or precursor cell,
   (b) culturing said immortalised cell in order to produce a homogeneous population of human chondroprogenitor cells,
   (c) activating the control means in order to terminate immortalisation and activate differentiation; and
   (d) allowing differentiation of said cells so as to produce fully differentiated human hypertrophic chondrocyte cells.

2. A method according to claim 2 wherein said immortalising gene is a viral oncogene.

3. A method according to claim 2 wherein said oncogene is a retroviral oncogene.

4. A method according to claim 3 wherein said control means is responsive to environmental conditions.

5. A method according to claim 1 wherein said immortalising gene and control means are integrated.

6. A method according to claim 5 wherein said integrated immortalisation gene and control means comprise a temperature sensitive entity.

7. A method according to claim 6 wherein said entity is an oncogene.

8. A method according to claims 6 or 7 wherein the immortalising gene is SV40T antigen.

9. A method according to claim 1 wherein the process of allowing differentiation of said cells comprises exposure to a differentiating agent.

10. A method according to claim 9 wherein said differentiating agent is Vitamin $D_3$.

11. A method according to claims 9 or 10 wherein said differentiating agent is Vitamin K, either alone or in combination with Vitamin $D_3$.

12. A method according to claim 9 wherein said differentiating agent, is dexamethasone.

13. A method according to claim 1 which method further comprises immortalisation of a human undifferentiated or precursor cell with an immortalising gene and also a safety means which enables selective disabling and/or destruction of said cell line.

14. A method according to claim 13 wherein said method involves transfection of said cell line with a gene which in the presence of certain agents produces a cytotoxic effect and/or product.

15. A method according to claim 14 wherein said gene is viral thymidine kinase.

16. A method according to claim 14 wherein said gene is cytosine deaminase.

17. A method according to claim 13 wherein transcription of the immortalising gene also results in transcription of the safety means.

18. Cells or cell lines produced in accordance with the method of claim 1.

19. Cells or cell lines according to claim 18 comprising at least one homogeneous population of immortalised cells provided with means to terminate immortalisation such that a homogeneous population of differentiated cells is provided.

20. Cells or cell lines according to claim 18 comprising at least one safety means which enables selective disabling and/or destruction of said cell line.

21. Cells or cell lines according to claim 19 comprising at least one safety means which enables selective disabling and/or destruction of said cell line.

\* \* \* \* \*

UNITED STATES PATENT AND TRADEMARK OFFICE
CERTIFICATE OF CORRECTION

PATENT NO.    : 6,340,592 B1  Page 1 of 1
DATED         : January 22, 2002
INVENTOR(S)   : Bradley Michael and John Stringer It is certified that error appears in the above-identified patent and that said Letters Patent is hereby corrected as shown below:

<u>Column 6,</u>
Line 28, after "FIG. 2", insert -- (Von Kossa staining control 33ºC microscopic view) --;
Line 30, after "FIG. 3", insert -- (Von Kossa staining microscopic view) --;
Line 33, after "FIG. 4" insert -- Macroscopic view of Von Kossa staining) --;
Line 34, after "clone", insert -- (Clone 7; bottom row of two cultures in Figure) and after "population", insert -- (top row of two cultures in Figure), and after "with" insert -- (right hand column of two culures in Figure),
Line 35, after "without", insert -- (left hand column of two cultures in the Figure) --;
Line 36, after "FIG.5"", insert -- (Macroscopic view of Von Kossa staining) --;
Line 37, after "clone", insert -- (Clone 7) -- and after "with" replace "Dex" with -- Dexamethasone --;
Line 44, after "percentage.", insert -- (In Figure 6: Error bars =SEM, n=4; All groups compared to control for statistical analysis (student's t- test) --;
Line 51, after "cells", insert -- (in Figure 7: Error bars=SEM, n=4; All groups compared to control for statistical analysis (student's t-test) --

Signed and Sealed this

Twenty-third Day of July, 2002

Attest:

*Attesting Officer*

JAMES E. ROGAN
*Director of the United States Patent and Trademark Office*